United States Patent
Suttin et al.

(10) Patent No.: US 10,922,447 B2
(45) Date of Patent: Feb. 16, 2021

(54) METHOD AND SYSTEM FOR SELECTING SURFACE FINISHES

(71) Applicant: BIOMET 3I, LLC, Palm Beach Gardens, FL (US)

(72) Inventors: Zachary B. Suttin, West Palm Beach, FL (US); Ross W Towse, San Marcos, CA (US)

(73) Assignee: Biomet 3I, LLC, Palm Beach Gardens, FL (US)

( * ) Notice: Subject to any disclaimer, the term of this patent is extended or adjusted under 35 U.S.C. 154(b) by 0 days.

(21) Appl. No.: 16/048,809

(22) Filed: Jul. 30, 2018

(65) Prior Publication Data

US 2018/0336291 A1 Nov. 22, 2018

Related U.S. Application Data (63) Continuation of application No. 13/742,432, filed on Jan. 16, 2013, now Pat. No. 10,061,868.

(60) Provisional application No. 61/705,816, filed on Sep. 26, 2012.

(51) Int. Cl.
*G06F 30/00* (2020.01)
*G16H 20/40* (2018.01)
*A61C 8/00* (2006.01)

(52) U.S. Cl.
CPC ...... *G06F 30/00* (2020.01); *A61C 2008/0046* (2013.01); *G16H 20/40* (2018.01)

(58) Field of Classification Search
CPC ..... A61C 13/0004; A61C 7/002; A61C 13/00; A61C 1/084; G06F 17/50; G06F 19/00; G06F 30/00; G05B 19/4097; G05B 2219/45167; G05B 19/4099; G05B 2219/35134; G05B 2219/35219; G06T 17/00; G06T 19/00; G06T 2200/24
See application file for complete search history.

(56) References Cited

U.S. PATENT DOCUMENTS

| | | | |
|---|---|---|---|
| 5,128,870 A | 7/1992 | Erdman et al. | |
| 6,558,162 B1 | 5/2003 | Porter et al. | |
| 8,425,231 B1* | 4/2013 | Hochman | A61C 8/008 433/173 |
| 2005/0048194 A1* | 3/2005 | Shmulewitz | A61F 2/82 427/2.24 |

(Continued)

OTHER PUBLICATIONS

"U.S. Appl. No. 13/742,432, Advisory Action dated May 24, 2016", 4 pgs.

(Continued)

*Primary Examiner* — Kenny A Cese
(74) *Attorney, Agent, or Firm* — Schwegman Lundberg & Woessner, P.A.

(57) ABSTRACT

A method and system of selecting a surface finish for a computer designed component associated with an anatomical area of a specific patient. A computer designed component is created. The component includes at least one surface. An interface of finishing software displays an image of the component and the at least one surface. A plurality of finishes available for the at least one surface is displayed. A selection of one of the plurality of finishes for the at least one surface is input by a user. The component data and finishing data may then be sent to a computer aided manufacturing system to manufacture the computer designed component.

20 Claims, 5 Drawing Sheets

(56) References Cited

U.S. PATENT DOCUMENTS

| | | | |
|---|---|---|---|
| 2005/0142517 A1* | 6/2005 | Frysh | A61C 9/0053 433/173 |
| 2008/0021584 A1 | 1/2008 | Whaite et al. | |
| 2008/0090207 A1 | 4/2008 | Rubbert | |
| 2008/0153067 A1 | 6/2008 | Berckmans et al. | |
| 2009/0130630 A1 | 5/2009 | Suttin et al. | |
| 2012/0022834 A1* | 1/2012 | Lajoie-Dorval | G16H 50/50 703/1 |
| 2012/0064489 A1* | 3/2012 | Rubbert | A61C 8/0006 433/175 |
| 2012/0065756 A1* | 3/2012 | Rubbert | A61C 13/0004 700/98 |
| 2013/0211531 A1 | 8/2013 | Steines et al. | |
| 2014/0088929 A1 | 3/2014 | Suttin et al. | |

OTHER PUBLICATIONS

"U.S. Appl. No. 13/742,432, Advisory Action dated Dec. 18, 2017", 3 pgs.
"U.S. Appl. No. 13/742,432, Final Office Action dated Jul. 20, 2017", 22 pgs.
"U.S. Appl. No. 13/742,432, Final Office Action dated Oct. 22, 2014", 17 pgs.
"U.S. Appl. No. 13/742,432, Final Office Action dated Dec. 16, 2015", 17 pgs.
"U.S. Appl. No. 13/742,432, Non Final Office Action dated Jan. 12, 2017", 17 pgs.
"U.S. Appl. No. 13/742,432, Non Final Office Action dated Jun. 13, 2014", 14 pgs.
"U.S. Appl. No. 13/742,432, Non Final Office Action dated Jul. 17, 2015", 15 pgs.
"U.S. Appl. No. 13/742,432, Notice of Allowability dated Jul. 18 2018", 8 pgs.
"U.S. Appl. No. 13/742,432, Notice of Allowance dated Apr. 24, 2018", 10 pgs.
"U.S. Appl. No. 13/742,432, Response filed Jan. 22, 2015 to Final Office Action dated Oct. 22, 2014", 12 pgs.
"U.S. Appl. No. 13/742,432, Response filed Apr. 12, 2017 to Non Final Office Action dated Jan. 12, 2017", 13 pgs.
"U.S. Appl. No. 13/742,432, Response filed Apr. 18, 2016 to Final Office Action dated Dec. 16, 2015", 12 pgs.
"U.S. Appl. No. 13/742,432, Response filed Jun. 16, 2016 to Final Office Acton dated Dec. 16, 2015", 13 pgs.
"U.S. Appl. No. 13/742,432, Response filed Jul. 30, 2014 to Non Final Office Action dated Jun. 13, 2014", 8 pgs.
"U.S. Appl. No. 13/742,432, Response filed Sep. 15, 2015 to Non Final Office Action dated Jul. 17, 2015", 10 pgs.
"U.S. Appl. No. 13/742,432, Response filed Dec. 4, 2017 to Final Office Action dated Jul. 20, 2017", 15 pgs.
"European Application Serial No. 13779431.9, Communication Pursuant to Article 94(3) EPC dated Feb. 22, 2018", 4 pgs.
"European Application Serial No. 13779431.9, Response filed Jul. 4, 2018 to Communication Pursuant to Article 94(3) EPC dated Feb. 22, 2018", 5 pgs.
"European Application Serial No. 13779431.9, Response filed Nov. 17, 2015 to Communication pursuant to Rules 161(1) and 162 EPC dated May 7, 2015", 6 pgs.
"International Application Serial No. PCT/US2013/061145, International Preliminary Report on Patentability dated Apr. 9, 2015", 7 pgs.
"International Application Serial No. PCT/US2013/061145, International Search Report dated Feb. 5, 2014", 3 pgs.
"International Application Serial No. PCT/US2013/061145, Written Opinion dated Feb. 5, 2014", 5 pgs.
U.S. Appl. No. 13/742,432, filed Jan. 16, 2013, Method and System for Selecting Surface Finishes.

\* cited by examiner

METHOD AND SYSTEM FOR SELECTING SURFACE FINISHES

TECHNICAL FIELD

The present disclosure relates generally to systems for fabricating custom dental components. More particularly, the present disclosure relates to a system for selection and application of surface finishes for a computer manufactured dental component.

BACKGROUND OF THE INVENTION

The recent era of digital dentistry has had a significant impact on the restorative methods used for conventional and implant dentistry. Technologies such as digital data acquisition, computer aided design (CAD), computer aided manufacturing (CAM) now exist that enable the clinician and laboratory to develop highly aesthetic patient-specific restorations. Traditionally, stock dental components (or a hand modified version of such components) were adapted to specific patients. Such traditional methods depended on manual measurement and tooling, and as a result were time consuming and suffered from accuracy issues. The traditional methods of manual measurement and tooling of a component are being replaced by virtually designed restorations based on digitally acquired anatomic datasets.

An example of computer aided design and manufacture of a customized dental component may be the dental restoration of a partially or wholly edentulous patient with artificial dentition. An incision is made through the gingiva to expose the underlying bone. An artificial tooth root, usually a dental implant, is placed in the jawbone for integration. The dental implant generally includes a threaded bore to receive a retaining screw holding mating components therein. During the first stage, the gum tissue overlying the implant is sutured and heals as the osseointegration process continues.

Once the osseointegration process is complete, the gum tissue is re-opened to expose the end of the dental implant. A healing component or healing abutment is fastened to the exposed end of the dental implant to allow the gum tissue to heal therearound. Preferably, the gum tissue heals such that the aperture that remains generally approximates the size and contour of the aperture that existed around the natural tooth that is being replaced. To accomplish this, the healing abutment attached to the exposed end of the dental implant has the same shape as the gingival portion of the natural tooth being replaced. The healing abutment is removed and an impression coping is fitted onto the exposed end of the implant. This allows an impression of the specific region of the patient's mouth to be taken so that an artificial tooth is accurately constructed. Thus, in typical dental implant systems, the healing component and the impression coping are two physically separate components. Preferably, the impression coping has the same gingival dimensions as the healing component so that there is no gap between the impression coping and the wall of the gum tissue defining the aperture. Otherwise, a less than accurate impression of the condition of the patient's mouth is made. The impression coping may be a "pick-up" type impression coping or a "transfer" type impression coping, both known in the art. After these processes, a dental laboratory creates a prosthesis to be permanently secured to the dental implant from the impression that was made.

In addition to the method that uses the impression material and mold to manually develop a prosthesis, systems exist that utilize scanning technology to assist in accurately generating a prosthesis. A scanning device is used in one of at least three different approaches. First, a scanning device can scan the region in the patient's mouth where the prosthesis is to be placed without the need to use impression materials or to construct a mold. Second, the impression material that is removed from the healing abutment and surrounding area is scanned. Third, a dentist or technician can scan the stone model of the dental region that was formed from the impression material and mold to produce the permanent components.

Three basic scanning techniques exist, laser scanning, photographic imaging and mechanical sensing. Each scanning technique is used or modified for any of the above-listed approaches (a scan of the stone model, a scan of the impression material, or a scan in the mouth without using impression material) to create the prosthesis. After scanning, a laboratory can create and manufacture the permanent crown or bridge, usually using a computer aided design (CAD) package.

The utilization of a CAD program is one method of creating a three dimensional model based on scanning a dental region. Preferably, after the impression is made of the patient's mouth, the impression material or stone model is placed on a support table defining the X-Y plane. A scanning laser light probe is directed onto the model. The laser light probe emits a pulse of laser light that is reflected by the model. A detector receives light scattered from the impact of the beam with the impression to calculate a Z-axis measurement. The model and the beam are relatively translated within the X-Y plane to gather a plurality of contact points with known location in the X-Y coordinate plane. The locations of several contact points in the Z-plane are determined by detecting reflected light. Finally, correlating data of the X-Y coordinates and the Z-direction contact points creates a digital image. Once a pass is complete, the model may be tilted to raise one side of the mold relative to the opposite vertically away from the X-Y plane. Subsequent to the model's second scan, the model may be further rotated to allow for a more accurate reading of the model. After all scans are complete, the data may be fed into a CAD system for manipulation of this electronic data by known CAD software.

Photographic imaging can also used to scan impression material, a stone model or to scan directly in the mouth. For example, one system takes photographs at multiple angles in one exposure to scan a dental region, create a model and manufacture a prosthetic tooth. This process is generally initiated with the process of taking a stereophotograph with a camera from approximately 50 to 150 mm away from the patient's mouth. The stereophotograph can involve a photograph of a patient's mouth already prepared with implantation devices. Correct spatial positioning of the dental implants is obtained by marking the implant in several locations. The resulting photograph presents multiple images of the same object. The images on the photographs are scanned with a reading device that digitizes the photographs to produce a digital image of the dental region. The data from the scanner is electronically transmitted to a graphical imaging program that creates a model that is displayed to the user. After identification of the shape, position and other details of the model, the ultimate step is the transmission of the data to a computer for manufacturing.

The third scanning technique uses mechanical sensing. A mechanical contour sensing device is used to read a dental model and produce a prosthetic tooth. The impression model is secured to a table that may rotate about its longitudinal axis as well as translate along the same axis with variable speeds. A mechanical sensing unit is placed in contact with the model at a known angle and the sensing equipment is held firmly against the surface of the model by a spring. When the model is rotated and translated, the sensing equipment can measure the changes in the contour and create an electronic representation of the data. A computer then processes the electronic representation and the data from the scanning device to create a data array. The computer then compresses the data for storage and/or transmission to the milling equipment.

While the current technologies provide a means by which to design and manufacture improved prosthetic restorations, the scope is limited to macro geometry, material type and color shade inputs. A post-processing step is therefore required to create a desirable surface finish (or a multitude of surface finishes) for a restoration component to facilitate needs such as aesthetics, plaque resistance, soft tissue preservation, and restorative retention. Adding to the complexity, this additional step of surface finish selection is open to artistic interpretation of the customer and needs/inputs by the dental laboratory and is limited by the fabrication techniques employed (typically hand manipulation). Thus, while the surface finishes can be modified subsequent to the component fabrication, this is restricted by (a) the ability of the customer to clearly communicate their needs and (b) the skill of the technician in being able to recreate the associated input(s) when fabricating the desired component.

As with the macro geometrical design, there is a need to predictably control (specify and produce) the surface finish so that the desired end state for a particular component is achieved. There is also a need to provide an accessible interface for a designer to designate finishes that may be accurately implemented by a tooling system to produce the desired finishes for the component surfaces. There is a further need for a visual interface allowing a designer to accurately designate finishes for the surfaces of a computer generated component.

SUMMARY

According to one example, a method of selecting a surface finish for a computer designed component associated with an anatomical area of a specific patient is disclosed. The computer designed component including at least one surface is created. An image of the component and the at least one surface is displayed. A plurality of finishes available for the at least one surface is displayed. A selection of one of the plurality of finishes for the at least one surface via a user interface is accepted.

Another example is a system to produce a customized component for a specific patient, the system. A storage device stores macro geometric data representing a component having at least one surface. A display displays a user interface showing an image of the component and the at least one surface. A controller displays a plurality of finishes available for the at least one surface and accepts a selection of one of the plurality of finishes for the at least one surface via the user interface.

Another example is a non-transitory, machine readable medium having stored thereon instructions for selection of finishes for a component designed specifically for a patient. The stored instructions include machine executable code, which when executed by at least one machine processor, causes the machine to create a computer designed component including at least one surface. The instructions cause the machine to further display an image of the component and the at least one surface. The instructions cause the machine to further display a plurality of finishes available for the at least one surface. The instructions cause the machine to further accept a selection of one of the plurality of finishes for the at least one surface via a user interface.

The foregoing and additional aspects and implementations of the present disclosure will be apparent to those of ordinary skill in the art in view of the detailed description of various embodiments and/or aspects, which is made with reference to the drawings, a brief description of which is provided next.

While the invention is susceptible to various modifications and alternative forms, specific embodiments thereof have been shown by way of example in the drawings and will herein be described in detail. It should be understood, however, that it is not intended to limit the invention to the particular forms disclosed but, on the contrary, the intention is to cover all modifications, equivalents, and alternatives falling within the spirit and scope of the invention as defined by the appended claims.

DESCRIPTION OF ILLUSTRATIVE EMBODIMENTS

Figure 1:
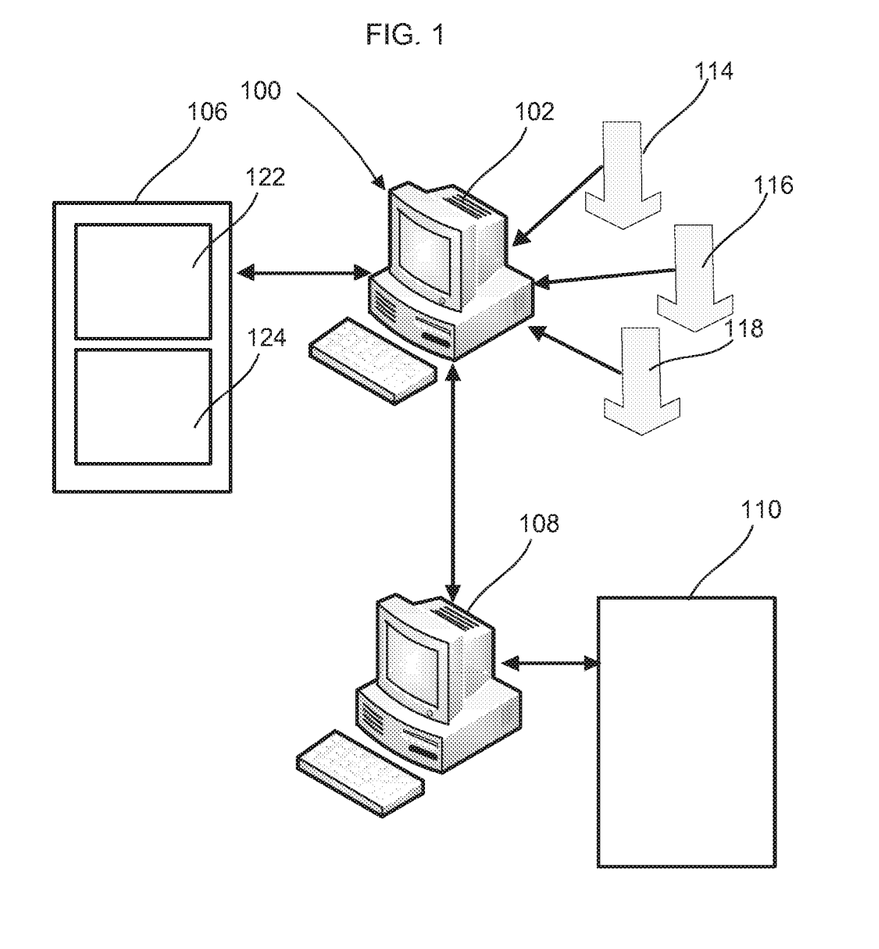
FIG. 1 is a block diagram of a system for designing and fabricating a dental component by computer aided design and manufacturing.

A computerized design and manufacturing system 100 for designing and manufacturing custom dental components is shown in FIG. 1. The system 100 is used to produce dental components such as bars, abutments, implants, crowns, and screws which are specifically tailored to a specific patient anatomy. The system 100 includes a computer aided design (CAD) workstation 102, a storage device 106, a computer aided manufacturing (CAM) workstation 108 and a tooling system 110. The CAD workstation 102 is used to create a three-dimensional model of a desired dental component. The CAD workstation 102 accepts and generates numerical data to fabricate the dental component which may be used by the CAM workstation 108 in conjunction with the tooling system 110 to produce the desired component and provide the appropriate finishes for various surfaces of the component.

The numerical data may be Obtained from a patient directly via a scanning device such as a three-dimensional laser scanner 112, a stereophotograph image scanner 114 for photographic imaging and a mechanical contour sensing device 116 for mechanical scanning. Other procedures to obtain numerical data may be used such as forming a cast of the patient and scanning a model produced from cast by one of three scanners described above. The scanners 112, 114 or 116 therefore output numerical data specific to the patient that may be used by the component designer to tailor a customized component to fit the desired anatomical areas of a patient.

The CAD workstation 102 is coupled to the storage device 106 which stores a library of template components 122 and a library of completed components 124. The template components in the template components library 122 are starting generic component types which a user may select and modify using the CAD software (i.e., 3shape, DentCAD, Exocad, etc.) to customize the dental component to the specific anatomical requirements of the patient. Each of the implants is an electronic file of macro geometric data representing a component having at least one surface. A user begins the macro geometrical design process by accessing a specific template matching the desired type of dental component from the template library 122. The user then imports patient specific numeric data that is gathered by scanning methods and tools such as the hand held three-dimensional scanner 112. For example, specialized software may further interpret the scanned numerical data to construct a three-dimensional visual model of the area that the dental component is to be inserted in order to further assist a component designer. The resulting component design is a macro geometric three-dimensional data representation of the desired component which incorporates the numerical data from the patient.

Following completion of the macro geometrical design phase for a dental component using the computer design software running on the CAD workstation 102, the user completes the component by specifying the surface finish requirements for different surfaces of the completed macro geometrical design using finish selection software running on a workstation such as the CAD workstation 102 in FIG. 1 as will be explained below. The design software allows for displaying an image of the component and the at least one surface of the component. A plurality of finishes available for the at least one surface is displayed. The software accepts a selection of one of the plurality of finishes for the at least one surface via a user interface as will be explained below.

The combined macro geometrical design and finishing data relating to a desired component is stored in the completed components library 124 as a component file and is passed to the CAM workstation 108 which controls the tooling system 110 to produce the physical component. The macro geometrical design data provides the dimensions for which a blank of material should be milled to produce the desired component shape. The selected finishing data provides additional instructions for finishing the surfaces of the component. For example, when a custom abutment is created, the design of the custom abutment and desired finishes from the CAD workstation 102 are input via the CAM workstation 108 into the tooling system 110. The tooling system 110 includes precision manufacturing machines such as a computer numerical control (CNC) milling machine, to create the custom abutment from a blank of suitable material for the component such as metal, usually titanium, or a titanium alloy, or a ceramic material. Additional machine technologies such as grit/sand blasting, physical vapor deposition, numeric controlled acid etching, numeric controlled nanoscale crystalline deposition, and numeric controlled anodization are controlled via the data from the CAM workstation 108 to provide the desired finishes to the surfaces of the component after completion of milling the blank into the component.

Figure 2A:
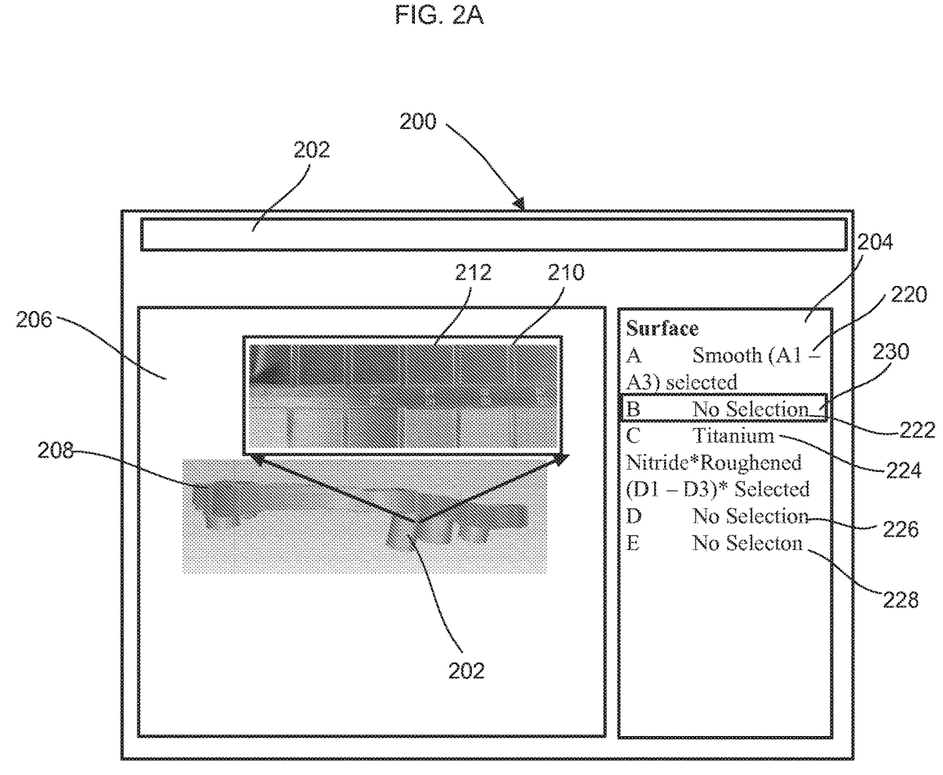
FIG. 2A is an interface display allowing a user to select surface finishes for dental components produced by the system in FIG. 1.

FIG. 2A shows an interface screen 200 that is generated by software for selection of finishes for component surfaces that is executed by the controller of the CAD workstation 102 in this example. Of course the finishing software may be run on any appropriate computing device. In this example, the interface screen 200 is displayed to the user on a display of the CAD workstation 102. The interface screen 200 serves as a user interface to display a plurality of finishes available for a surface on a component. The interface screen 200 also allows a user to designate the desired finishes for different surfaces of the dental component generated by the CAD program on the CAD workstation 102. The data for the selected finishes is stored with the component data file for later manufacturing of the physical component. The interface display 200 includes a control menu 202 that allows a user to access various component files from the template library 122 or the completed components library 124 in FIG. 1. The control menu 202 also may include command selections that allow the creation and saving of new component files, the control of different selections, the manipulation of data and other functions. The selection of a component file from the template library 122 or the completed components library 124 allows a user to display a list of surfaces specific to that component in a side surface data window 204. The component design is shown in three-dimensional image form in a component window 206. An example component image 208 of a dental bar is shown in FIG. 2A. A library of available surface finishes available for the component designer to select from for each surface of the component 208 that requires finishing is accessed via the interface display 200. One possible interface is a pop-up window 210 which includes a palette 212 that displays finish selections available for a selected surface. Of course other interfaces such as menu selections accessible by a menu bar such as the control menu 202 or pop-up menus could be provided by the interface 200 to show finish selections. In addition, the various controls, windows and functions of the interface 200 may have any arrangement to facilitate user accessibility and ease and are not limited to the example shown in FIG. 2A.

The component window 206 shows a three-dimensional image of the desired component which may be generated by the CAD application as explained above. The component window 206 in this example shows the three-dimensional image 208 of the CAD created dental component which is a customized dental bar used in a dental restoration process. The image 208 may be rotated by rotational controls or by other user input devices such as a mouse. The user may select surfaces on the image 208 for the selection of finishes. In this example, a user may use a mouse and select various surfaces on the image 208 that require non-default finishes. These surfaces may be highlighted or have a different color or shading to indicate their selection. By rotating the image 208, all of the component surfaces may be shown to the user. Thus, all of the surfaces of the dental component represented by the image 208 may be shown and therefore selected by a user for finish selection.

Each dental component designed by a user may have a variety of surfaces that require finishing instructions and corresponding finishing data that are assigned by a user via the interface 200. The selections in the palette 212 in the pop-up window 210 show finishes that are available for the surface by selection of the user. The surfaces for each component are listed in the surface data window 204 which shows each surface in entries 220, 222, 224, 226 and 228 and the selected finishes for each surface if applicable. For example, the surface represented by entry 220 has been assigned a smooth finish. For surfaces for which a finish has not been selected, the surface entry indicates that a finish has not been selected such as for surface entry 226. Alternatively, a default finish may be assigned to each surface initially. The default finish is the finish for that surface if a user does not select a specialized finish. In this example, a box 230 is used to highlight the surface name which is selected on the image 208 in the component window 206. Each surface may include a descriptive designation for convenience in the surface data window 204 and or on the image 208 or elsewhere in the interface 200. The designations may include a specific descriptive title, a numerical or character code, etc.

As explained above, the pop-up window 210 may have a default setting for the recommended or default finish for each surface in the palette 212. Other finish options may be available within other menus displayed or accessed on the interface 200. Further, the available finishes may be based on the location or the size of the component surface. Additionally, where applicable, the user may have the option of using a slider when selecting a finish type that can be further modulated by selection of specific values within a range of values for the finish. For example, a user may select between surface area roughness (Sa) values of 0.05, 0.1, 0.5, 2, 3, 10, 20 μm, etc. using a slider control. Alternatively, a user may input specific numerical values for the finish.

Figure 2B:
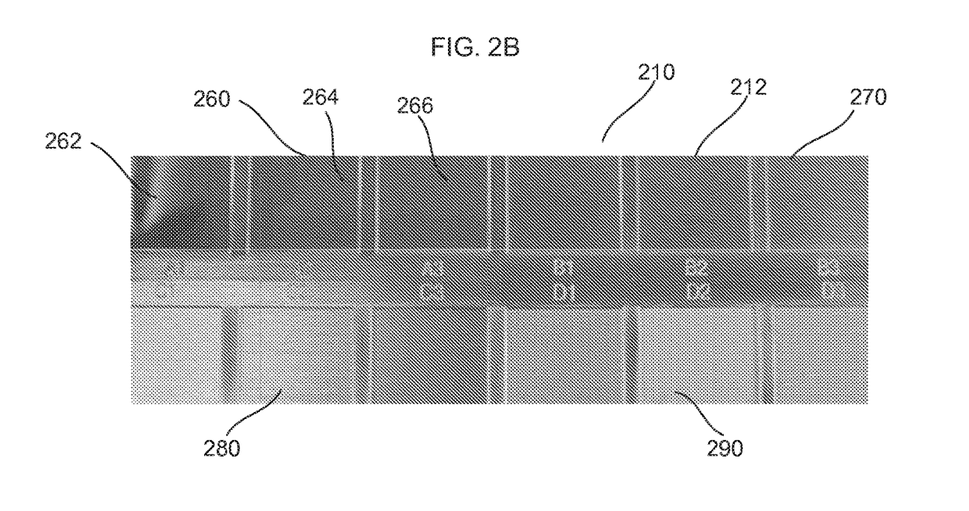
FIG. 2B is a close-up view of an example finish palette presented to a user in the interface display in FIG. 2A in order to select a finish for a selected surface.

FIG. 2B shows a close up of the example pop-up window 210 and the corresponding palette 212 with finishes available for a selected surface in FIG. 2A. The appropriate finishes for a particular surface are stored and selected by the finishing software for display as selections when a particular surface is selected by the user. The selections on palette 212 may be modified by a user to create customized finishes. Such customized finishes may be saved and offered as a selection for similar component surfaces. One example of such a customized selection is a user designated specific numerical value for a finish. Another example could be the combination of various processing steps and/or the order of application of such steps to the surface as designated by a user.

In the example in FIG. 2B, the palette 212 displays four general finishes in selection areas 260, 270, 280 and 290. In this example, the finishes are designated as tool and mold standard finishes which are A finishes in area 260 which are smooth finishes, B finishes in area 270 which are smooth finishes, C finishes in area 280 which are roughened finishes, and D finishes in area 290 which are another class of roughened finishes. Of course any variety or number of finishes may be displayed that are appropriate for the selected surface. As may be seen in FIG. 2B, each selection area 260, 270, 280, and 290 includes graphics showing the appearance of the finish option as well as text describing each finish. Each selection area may also have multiple selections corresponding to different degrees of the finish which may be specifically selected. For example, the finish area 260 representing A finishes (smooth) has an A1 selection 262, an A2 selection 264 and an A3 selection 266. In this example, A1-A3 represent different diamond buff finishes, B1-B3 represent different paper grit finishes, C1-C3 represent different stone finishes, and D1-D3 represent different dry blasted finishes.

After the user selects the surface on the dental component image 208 and the finish for the surface, the CAD workstation 102 stores the selections for final finishing data of the dental component in the component file. The selected surface finish data is used by the CAM workstation 108 to be applied to the surface via the tooling system 110 in the manufacturing process.

Similar to the numerical data being stored during the design phase so that it can be reproduced in the subsequent CAM operations, the corresponding surface finishes are logged and then recreated in the computer controlled manufacturing process performed by the system 100 in FIG. 1. Algorithms run by the CAM workstation 108 control the associated operating variables (i.e., tooling, machine speeds, machine feed rates, etc.) for the tooling system 110 to apply the various surface finishes selected by the user of the CAD workstation 102. Although the above examples relate to surface finishes resulting from mechanical operations (i.e., machining, blasting, etc.), chemical and/or other potentially subtractive or additive processes could also be programmed and loaded for the CAM workstation 108 (i.e., physical vapor deposition (PVD), acid etching, anodizing, deposition, etc.) to further provide additional manufacturing steps for application to the surfaces of the dental component.

Figure 3A:
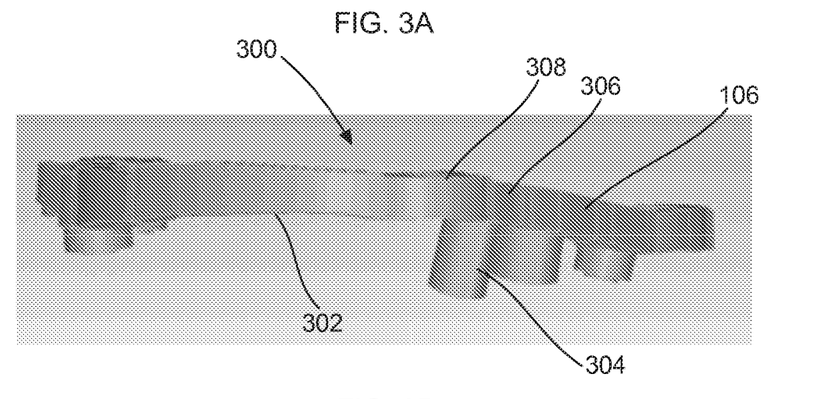
FIG. 3A is a perspective diagram of a resulting example dental bar component created by the CAD workstation in FIG. 1.

FIG. 3A shows an example dental component which is an image of a CAD generated implant bar 300 as shown in the component window 206 of the interface 200 in FIG. 2. The implant bar 300 is generated by a CAD workstation such as the CAD workstation 102 in FIG. 1 using numerical data obtained through the scanning methods described above and user design input. In this example, the bar 300 is used as a superstructure to create a full arch restoration based on a specific patient's jaw which requires restoration. The numerical data relating to the patient's jaw is obtained by scanning the edentulous areas of the jaw and incorporated in the design of the bar. More detail relating to the design of the implant bar 300 in FIG. 3A is disclosed in co-pending application Ser. No. 12/271,517 filed Nov. 5, 2008 and is hereby incorporated by reference in its entirety.

A 3D CAD model of the patient's mouth allows a practitioner to determine locations to place the implants to be utilized, and also allows the practitioner to select particular implants to use on the patient and therefore design the appropriate customized dental bar 300. First, by analyzing the patient's particular anatomical structure, the practitioner determines desired locations for implants. Based on the patient's anatomical structure at the desired locations, a practitioner selects an implant to be placed within the patient. As the general ranges for material properties for Type I-Type IV bone are known, the 3D CAD model of the bones of the patient are assigned material properties. The assigning of material properties may be performed automatically by software based on the results of the CT scan, or a practitioner may analyze the CT scan and assign material properties to the 3D CAD model of the patient based on what is shown on the CT scan. Based on output from CT scan, such as the number of Hounsfield's units obtained from the CT scan, a bone type may be obtained.

The CAD workstation 102 accesses a library of dental implants and other restorative components from a library such as the template library 122 that a practitioner may choose from when developing a treatment plan for a patient. The practitioner selects a proposed implant to use within a first implant site of the patient using the CAD software running on the CAD workstation 102. As explained above, the storage device 106 contains a library of templates 122 that includes dental implants, so that 3D models exist of the various implants that a practitioner may select. The selection of a proposed implant also causes the CAD software to create an osteotomy for the selected implant at the first implant site of the 3D CAD model. The resulting selected implants and implant sites are incorporated in the design of the implant bar 300 that is specifically tailored to incorporate the numerical data specific to the patient's jaw noted above.

The implant bar 300 is the result of a completed digital file prepared using the CAD workstation 102. The surface finishes for each of the surfaces of implant bar 300 are selected via the interface 200 and may be directly sent to the CAM workstation 108. The resulting combined macro geometric data and finishing/manufacturing data is transferred to the CAM workstation 108 in FIG. 1 for actual production via the tooling system 110. Since the finishes are selected from known instructions for the desired finishes, this avoids communication errors from the designer to the manufacturer and also results in accurate application of the desired finishes in producing the physical component.

In this example, there are four different surfaces 302, 304, 306, and 308 on the implant bar 300. In this example, the surface 302 is the bottom surface of the bar 300, the surface 304 is the side surfaces of the bar 300, the surface 306 is the surface of the implant interfaces and the surface 308 is the top surface of the bar 300. Of course it is to be understood that there may be many other different surfaces that may be shown by increasing the resolution of the component in order to identify or select sub-surfaces, free form surfaces, etc. Since the bar 300 is typically fabricated from metals, the finishes for each of the surfaces 302, 304, 306 and 308 are specific to metal and may be specialized for the type of metal used. A user may select finishes for each of the different surfaces 302, 304, 306, and 308 using the interface 200 shown in FIG. 2A. In this example, each specific surface for the dental bar 300 has a default finish which is preselected for the particular surface. The default finish for any surface may be changed by the user interface 200. Table 1 below shows examples of different finishes which may be provided for each surface. In this example, the entries in Table 1 and Table 2 below with an asterisk indicate that the surface finish type may be "fine-tuned" in terms of roughness and/or color with a slider scale.

TABLE 1

| Surface Finish | Surface 302 | Surface 304 | Surface 306 | Surface 308 |
|---|---|---|---|---|
| Default | *Smooth (A1-A3) | *Smooth (A1-A3) | *Roughened (C1-C3) | *Roughened (C1-C3) |
| Option 1 | *Roughened (C1-C3) | Titanium Nitride | *Roughened (D1-D3) | *Roughened (D1-D3) |
| Option 2 | *Roughened (D1-D3) | *Roughened (D1-D3) | *Roughened (grit blast) | *Roughened (grit blast) |
| Option 3 | *Roughened (grit blast) | Roughened (Acid Etch) | *Anodized | *Anodized |
| Option 4 | *Anodized | Nano CaP Deposition | *Retention Grooves | *Retention Grooves |
| Option 5 | *Retention Grooves | Nano CaP Deposition + Acid Etch | *Roughened (D1-D3) + *Retention Grooves | *Roughened (D1-D3) + *Retention Grooves |
| Option 6 | *Roughened (D1-D3) + *Retention Grooves | *Anodized | *Smooth (A1-A3) | *Smooth (A1-A3) |

Figure 3B:
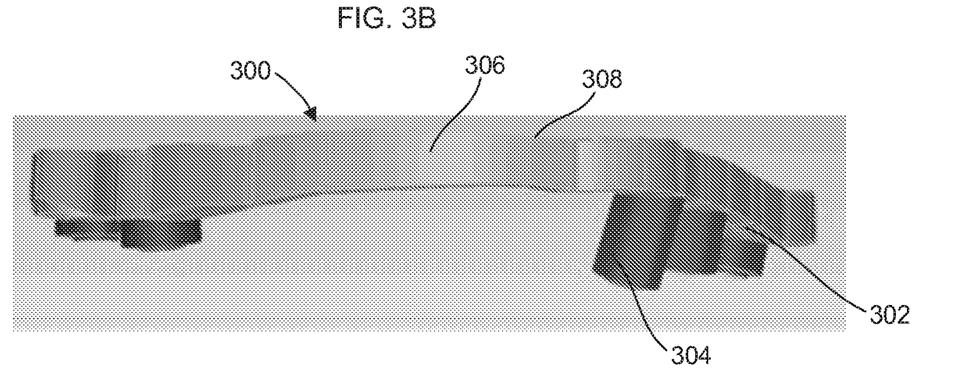
FIG. 3B is a display of the dental bar in FIG. 3A where certain surfaces are highlighted via the interface in FIG. 2A.

Each of the surfaces 302, 304, 306 and 308 of the bar 300 may be highlighted by the user of the interface software. For example, FIG. 3B shows the surfaces 304 of the implant sockets of the bar 300 highlighted by changing the color of the surface 304 indicating that a user is selecting the appropriate finish for the surfaces 304. As explained above, the bar 300 is shown in three-dimensional form to assist the user in viewing the surfaces that require selection of finishes. As shown in Table 1 above, there may be several options for the surfaces 304. The default option for the surfaces 304 is one of three smooth surfaces A1-A3. Other options may include a Titanium Nitride finish, a roughened finish (C1-C3 or D1-D3), a roughened finish with acid etching, a nano CaP deposition finish, a combined acid etching and nano CaP deposition finish and an anodized finish. As may be seen, the finish selections may incorporate combinations of finishing processes if desired. The bar 300 may be rotated to show different surfaces to assist the user in selecting finishes.

Figure 3C:
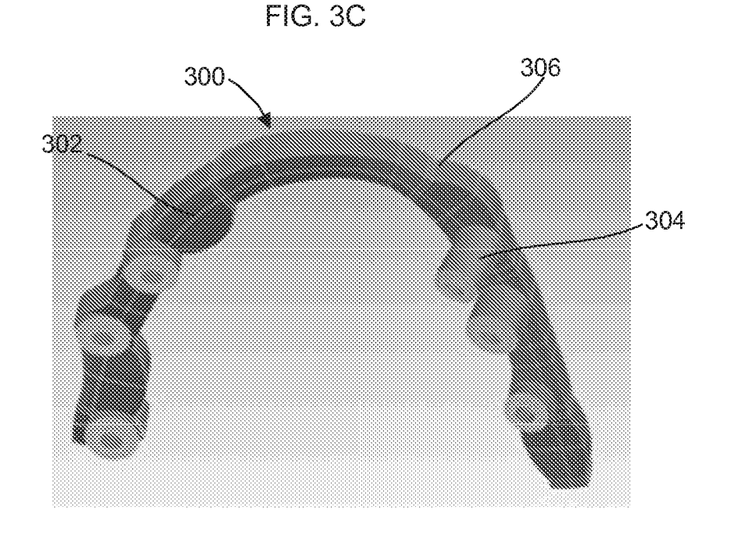
FIG. 3C is a display of the dental bar in FIG. 3A where certain additional surfaces are highlighted via the interface in FIG. 2A.

FIG. 3C shows the bar 300 rotated to better show the bottom surface 302. The bottom surface 302 is highlighted in FIG. 3C indicating that the user is selecting the finish for that surface. As shown in Table 1 above, the default option for the bottom surface 302 is one of three smooth surfaces A1-A3. The other options include different degrees of roughened surfaces, roughened finish using grit blast, anodized or retention grooves.

A further option for components with multiple elements may be to isolate each surface of each component element. For example, the interface 200 may allow a user to assign each of the socket surfaces 304 a different surface finish.

Figure 4A:
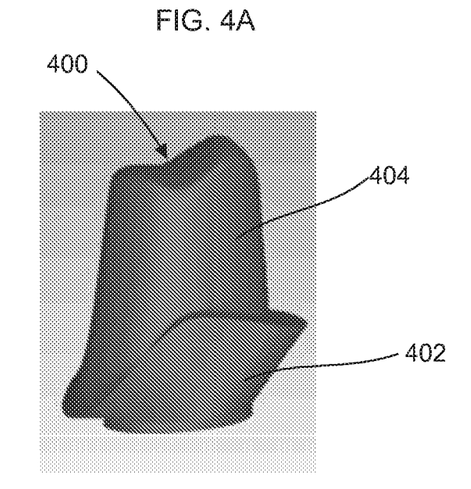
FIG. 4A is a perspective diagram of an abutment component created by the CAD workstation in FIG. 1.

Another example dental component is shown in FIG. 4A which shows a dental abutment 400 that is formed from digital data generated from the CAD workstation 102 in FIG. 1. The abutment 400 in FIG. 4A is formed in accordance with the method disclosed in co-pending application Ser. No. 12/070,922 filed Feb. 22, 2008 which is hereby incorporated by reference.

The numerical data used to create the abutment 400 is obtained by preparing a stone cast of the patient area with a healing abutment in this example. The cast is scanned using a scanning technique such as the handheld scanner, the laser scanner or the stereophotographic scanner. The scanned data is transferred into a graphical imaging program, such as the CAD software running on the CAD workstation 102 in FIG. 1 so that a three-dimensional CAD model of the stone cast is created. The CAD model of the stone cast is modified to create a first modified CAD model that removes the healing abutment of that the position of an implant, or the top surface of an implant, underlying the healing abutment is displayed.

The CAD program on the CAD workstation 102 is used to design a custom, patient specific, abutment 400 adapted to attach to the implant. The custom abutment 400 supports a final prosthesis, often referred to as a crown. A modified version of the stone model may be used to design the crown to fit between the adjacent teeth based on the specific dimensions and conditions of a patient's mouth. Thus, obtaining an accurate position of the dental implant is critical to designing an accurate crown. Once the CAD program on the CAD workstation 102 has been used to design a custom abutment, the design of the custom abutment 400 is input into a precision manufacturing system such as the tooling system 110. In the example of the abutment, the tooling system 110 may include a CNC milling machine, to create the custom abutment 400 from a blank of metal, usually titanium, or a titanium alloy, or from a ceramic material.

After the initial abutment is designed by the use of the CAD program on the CAD workstation 102, the abutment 400 is displayed on the interface 200 in FIG. 2A as shown in FIG. 4A. As shown in FIG. 4A, the abutment 400 has two different surfaces 402 and 404 that may be provided different final finishes to facilitate considerations such as aesthetics, plaque resistance, soft tissue preservation, and restorative retention. In this example, the selection of finishes for the surfaces 402 and 404 may depend on the material used for the abutment. For example if the abutment 400 is fabricated from a ceramic material such as yttria stabilized polycrystalline tetragonal zirconia (YTZP) ceramic, the finishes available are tailored toward ceramics. Other finishes may be available if a metal such as titanium is used for the abutment. Still other finishes may be available if the abutment is fabricated from a composite material or if the abutment is partially fabricated from titanium for certain elements and ceramic for other elements.

In this example, the surface 402 is the underside of the abutment that interfaces with the implant while the upper surface 404 interfaces with the prosthetic such as a crown. In this example, the finishes for each surface 402 and 404 are shown in Table 2.

TABLE 2

| Surface Finish | Surface 402 | Surface 404 |
|---|---|---|
| Default | *Smooth (A1-A3) | *Roughened (D1-D3) |
| Option 1 | Titanium Nitride | Titanium Nitride |
| Option 2 | *Roughened (D1-D3) | *Roughened (C1-C3) |
| Option 3 | Roughened (Acid Etch) | *Retention Grooves |
| Option 4 | Nano CaP Deposition | *Roughened (D1-D3) + *Retention Grooves |
| Option 5 | Nano CaP Deposition + Acid Etch | *Retention Grooves + Titanium Nitride |
| Option 6 | *Anodized | *Anodized |

Figure 4B:
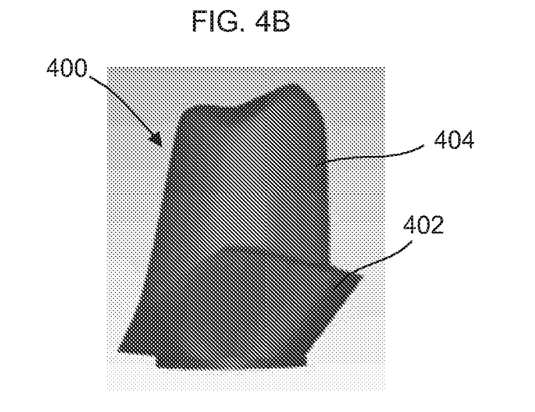
FIG. 4B is a display of the abutment in FIG. 4A where certain surfaces are highlighted via the interface in FIG. 2A.

FIG. 4B shows the surface 402 selected via the interface 200 of the abutment 400. As shown in FIG. 4B, the surface 402 is shown in a different color to indicate that the surface has been selected. As shown in Table 2, the default finish which will be displayed to the user is a smooth finish which may have several different graduations. The default option results in the selection of an "A1" finish on the highlighted surface 402, Other finish options for the surface 402 may include titanium nitride, roughened with acid etch, nano CaP deposition, nano CaP deposition in combination with an acid etch and anodization.

Figure 4C:
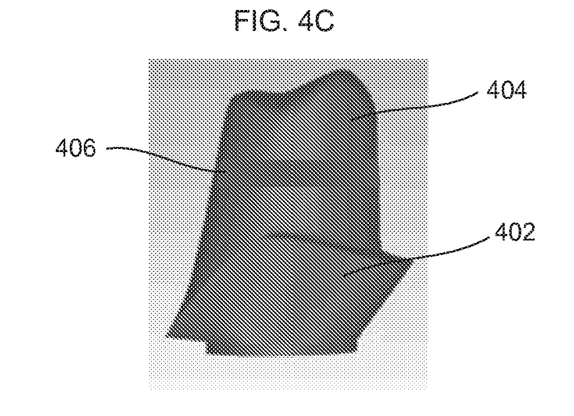
FIG. 4C is a display of the abutment in FIG. 4A where certain surface features to be applied to a surface are highlighted via the interface in FIG. 2.

The machining of physical features as may be required by the function of the component may also be selected for the surface. For example, FIG. 4C shows a cement retention groove feature 406 which may be applied on the surface 404. As shown in FIG. 4C, the user interface 200 may include selections for special milling instructions to be applied to a selected surface such as grooving, notches, etc. that may be appropriate to better retain cement for attaching a crown to the upper part of the abutment 400 at the surface 404.

Figure 5:
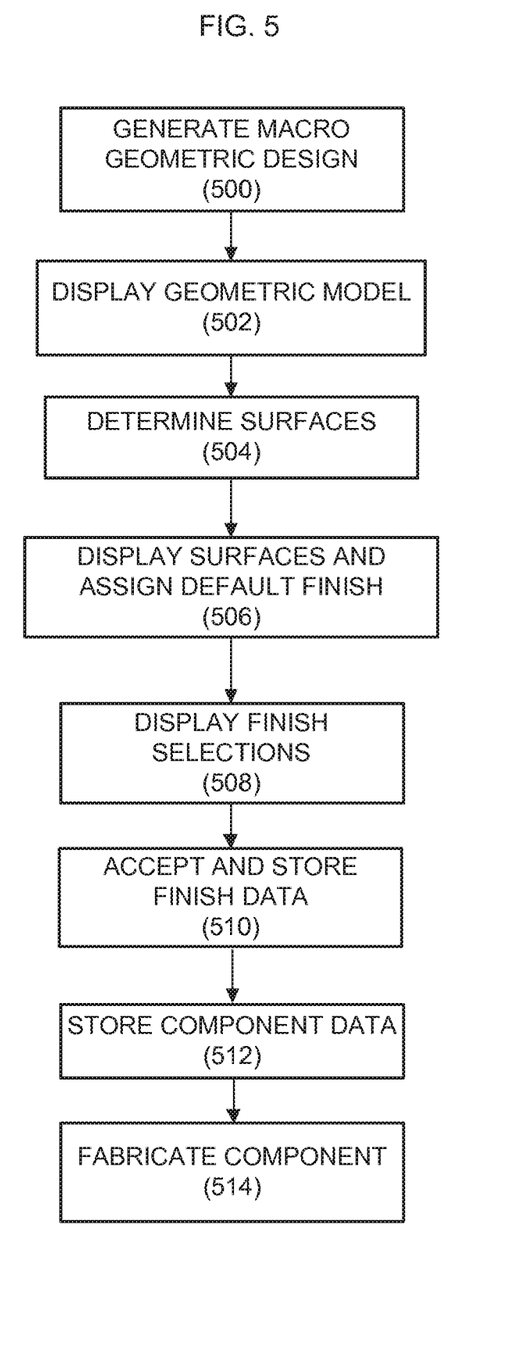
FIG. 5 is a block diagram of the process of selecting finishes for a computer designed dental component for fabrication by a computer aided manufacturing system.

The operation of the example process to select finishes for surfaces on components such as dental components shown in FIGS. 1-2, which can be nm on the CAD workstation 102 in FIG. 1, will now be described with reference to FIGS. 1-2 in conjunction with the flow diagram shown in FIG. 5. The flow diagram in FIG. 5 is representative of example non-transitory machine-readable instructions for implementing the processes described above to select finishes for surfaces of a computer aided designed dental component. In this example, the machine readable instructions comprise an algorithm for execution by: (a) a processor, (b) a controller, and/or (c) one or more other suitable processing device(s). The algorithm can be embodied in software stored on tangible and non-transitory media such as, for example, a flash memory, a CD-ROM, a floppy disk, a hard drive, a digital video (versatile) disk (DVD), or other memory devices, but persons of ordinary skill in the art will readily appreciate that the entire algorithm and/or parts thereof could alternatively be executed by a device other than a processor and/or embodied in firmware or dedicated hardware in a well-known manner (e.g., it may be implemented by an application specific integrated circuit (ASIC), a programmable logic device (PLD), a field programmable logic device (FPLD), a field programmable gate array (FPGA), discrete logic, etc.). For example, any or all of the components of the CAD workstation 102 in FIG. 1 could be implemented by software, hardware, and/or firmware. Also, some or all of the machine readable instructions represented by the flowchart of FIG. 5 can be implemented manually. Further, although the example algorithm is described with reference to the flowchart illustrated in FIG. 5, persons of ordinary skill in the art will readily appreciate that many other methods of implementing the example machine readable instructions can alternatively be used. For example, the order of execution of the blocks can be changed, and/or some of the blocks described can be changed, eliminated, or combined.

A numerical data representation associated with the anatomical area of the patient for the desired component is generated by taking into account the numerical data obtained through scans of a patient or scans of a cast taken from a patient. The macro geometrical data for the customized component is derived from selection of a template from the template library 122 in FIG. 1 and user input incorporating the numerical data associated with the patient (500). The (program then displays the intermediate component to the user in a three-dimensional display such as the image 208 in the component window 206 in FIG. 2A (502). The program determines surfaces of the designed component that require finishing data (504). The user may also designate the surfaces of the desired component that requiring finishing data. The program then displays each surface, determines appropriate finish selections for the surface and assigns a default finish to each of the surfaces (506).

The interface 200 then displays finish selections to the user for each of the surfaces for a particular component (508). The interface 200 then accepts selections for a user for finishes for each of the surfaces (510). The finish selections are then stored in the storage device 106 to complete the component file in the completed component library 124 (512). The completed data and finishing data are then passed to the CAM workstation 108 for fabrication of the component (514).

Although the previous examples relate to the selection of surface finishes for a dental, bar and a dental abutment, it is to be understood that other dental components such as screws, implants, healing abutments, temporary prostheses, crowns, copings, frameworks, permanent prostheses may be created and fabricated using the surface finish selection interface 200 described above. Further, it is to be understood that although the examples above relate to dental components, other components relating to anatomical restoration may be created and fabricated using the processes described above. For example, surface finishes may be selected for patient specific components such as knee, hip, jaw, shoulder, ankle, and spinal implants. It is to be understood that the user interface described above identifies the logical geometric transitions and defines the resultant surfaces of the component. However, another option is to allow a user to select free form surfaces with a tool such as a virtual paint brush on the interface 200. The user can in select as many finite surfaces of the components as desired. Of course, there are limitations associated with each surface finish and a warning system might be activated if the user violates certain rules associated with specific surface finishes when selecting surfaces.

While particular embodiments and applications of the present invention have been illustrated and described, it is to be understood that the invention is not limited to the precise construction and compositions disclosed herein and that various modifications, changes, and variations may be apparent from the foregoing descriptions without departing from the spirit and scope of the invention as defined in the appended claims.

What is claimed is:

1. A method of selecting a surface finish for a computer designed component associated with an anatomical area of a specific patient, comprising:
   creating the computer designed component including an outer surface;
   displaying an image of the component and the outer surface;
   accepting a first input from a user that defines a first portion of the outer surface;
   displaying, based on the first input from the user, a first plurality of available surface roughness finishes for the first portion of the outer surface from a plurality of surface roughness finishes, wherein a number of the first plurality of available surface roughness finishes for the first portion of the outer surface is less than a total number of the plurality of surface roughness finishes;
   accepting a first selection of one of the first plurality of available surface roughness finishes for the first portion of the outer surface via a user interface;
   accepting a second input from a user that defines a second portion of the outer surface;
   displaying, based on the second input from the user, a second plurality of available surface roughness finishes for the second portion of the outer surface from the plurality of surface roughness finishes, wherein a number of the second plurality of available surface roughness finishes for the second portion of the outer surface is less than the total number of the plurality of surface roughness finishes, and wherein the first plurality of available surface roughness finishes displayed for the first portion includes at least one surface roughness finish that is different from at least one surface roughness finish included in the second plurality of available surface roughness finishes displayed for the second portion;
   accepting a second selection of one of the second plurality of available surface roughness finishes for the second portion of the outer surface via a user interface.

2. The method of claim 1, wherein the component is one of a dental bar, dental abutment, dental implant, dental screw or dental crown.

3. The method of claim 1, wherein the first and second plurality of available surface roughness finishes are selected based on the material of the component.

4. The method of claim 1, wherein the first and second plurality of available surface roughness finishes are selected based on the location or the size of the portion of the outer surface.

5. The method of claim 1, wherein the user interface is a graphical user interface displaying a three-dimensional representation of the component and graphics representing the first and second plurality of available surface roughness finishes.

6. The method of claim 1, wherein one of the plurality of available surface roughness finishes accepts a value input from a slider interface.

7. The method of claim 1, further comprising:
   storing a file including the computer designed component and the surface roughness finishing selections; and
   sending the file to a computer aided manufacturing system for manufacturing the component.

8. The method of claim 1, wherein the selections for the surface roughness finishes include at least one of an additive finish or a subtractive finish.

9. The method of claim 1, wherein the outer surface includes a plurality of pre-defined surface portions that are selectable by a user.

10. The method of claim 9, wherein, upon selection by the user, a plurality of available surface roughness finishes are displayed for each of the plurality of pre-defined surface portions of the outer surface.

11. The method of claim 1, further comprising analyzing the image and determining the location of the portion of the outer surface.

12. The method of claim 1, wherein the component is created from a template component.

13. The method of claim 1, wherein the component is created by incorporating numerical data obtained from the specific patient.

14. The method of claim 10, wherein at least one of a first plurality of surface roughness finishes displayed for a first pre-defined surface portion of the outer surface defined by the user is different from a second plurality of surface roughness finishes displayed for a second pre-defined surface portion of the outer surface defined by the user.

15. A system to produce a customized component for a specific patient, the system comprising:
   a storage device to store macro geometric data representing a component having an outer surface;
   a display to display a user interface showing an image of the component and the outer surface;
   a processor in communication with the storage device and the display, the processor configured to:
      accept an input from a user that defines a portion of the outer surface;
      determine based on the input from the user a number of available surface roughness finishes from a plurality of surface roughness finishes stored on the storage device wherein the number of the available surface roughness finishes is less than a total number of the plurality of surface roughness finishes stored on the storage device, and wherein the number of available surface roughness finishes are surface roughness finishes that are compatible with the portion of the outer surface defined by the user; and
      display, based on the input from the user, the plurality of available surface roughness finishes for the portion of the outer surface from plurality of surface roughness finishes; and accept a selection of one of the plurality of available surface roughness finishes for the portion of the outer surface via the user interface.

16. The system of claim 15, wherein the number of available surface roughness finishes displayed is based on the material of the component.

17. The system of claim 15, wherein the number of available surface roughness finishes displayed is based on the location or the size of the portion of the outer surface.

18. The system of claim 15, wherein the user interface is a graphical user interface displaying a three-dimensional representation of the component and graphics representing the plurality of finishes.

19. The system of claim 15, wherein one of the plurality of surface roughness finishes accepts a value input from a slider interface.

20. A method of selecting a surface finish for a computer designed component associated with an anatomical area of a specific patient, comprising:

creating the computer designed component including an outer surface;

displaying an image of the component and the outer surface;

accepting an input from a user that defines a portion of the outer surface;

analyzing a plurality of surface roughness finishes to determine a number of the plurality of surface roughness finishes that are compatible with the portion of the outer surface defined by the user;

displaying, based on the input from the user, the number of the plurality of surface roughness finishes, wherein the number of the plurality of surface roughness finishes is less that a total number of the plurality of surface roughness finishes analyzed; and accepting a selection of one of the plurality of surface roughness finishes for the portion of the outer surface via a user interface.

* * * * *

UNITED STATES PATENT AND TRADEMARK OFFICE
CERTIFICATE OF CORRECTION

PATENT NO. : 10,922,447 B2  
APPLICATION NO. : 16/048809  
DATED : February 16, 2021  
INVENTOR(S) : Suttin et al.

Page 1 of 1

It is certified that error appears in the above-identified patent and that said Letters Patent is hereby corrected as shown below:

In the Claims

In Column 14, Line 54, in Claim 15, delete "determine" and insert --determine,-- therefor In Column 14, Line 54, in Claim 15, delete "user" and insert --user,-- therefor In Column 14, Line 57, in Claim 15, delete "device" and insert --device,-- therefor Signed and Sealed this  
Eighteenth Day of May, 2021

Drew Hirshfeld  
*Performing the Functions and Duties of the*  
*Under Secretary of Commerce for Intellectual Property and*  
*Director of the United States Patent and Trademark Office*